United States Patent [19]

Reynolds

[11] Patent Number: 4,504,585
[45] Date of Patent: Mar. 12, 1985

[54] AFFINITY IMMUNOASSAY SYSTEM

[75] Inventor: Robert A. Reynolds, Escondido, Calif.

[73] Assignee: Aalto Scientific, Ltd., San Marcos, Calif.

[21] Appl. No.: 364,031

[22] Filed: Apr. 5, 1982

[51] Int. Cl.[3] .................... G01N 33/54; G01N 33/56
[52] U.S. Cl. ..................................... 436/518; 436/528; 436/529; 436/531; 436/804; 436/822; 436/823; 435/4; 435/7
[58] Field of Search ................... 424/1, 1.5; 23/230 B; 436/501, 518–535, 542, 500; 435/178, 180, 4, 7

[56] References Cited

U.S. PATENT DOCUMENTS

| | | | |
|---|---|---|---|
| 4,125,492 | 11/1978 | Cuatrecasas et al. | 260/9 |
| 4,145,406 | 3/1979 | Schick et al. | 424/1 |
| 4,225,487 | 9/1980 | Cuatrecasas et al. | 260/121 |
| 4,231,999 | 11/1980 | Carisson et al. | 424/1 |
| 4,247,540 | 1/1981 | Holzmann | 424/95 |
| 4,248,965 | 2/1981 | Mochida et al. | 424/1 |
| 4,289,747 | 9/1981 | Chu | 424/1 |

OTHER PUBLICATIONS

Engvall, E. et al., Int. Journal of Cancer, vol. 20, pp. 1–5 (1977).
Engvall, E. et al., J. of Experimental Medicine, pp. 1584–1595 (1978).
Engvall, E. et al., Methods in Enzymology, vol. 20, pp. 419–439 (1980).

Primary Examiner—Christine M. Nucker
Assistant Examiner—M. Moskowitz
Attorney, Agent, or Firm—Brown, Martin & Haller

[57] ABSTRACT

An affinity immunoassay system in which a solid phase nonimmunological, group-specific ligand is used to insolubilize the analyte of interest either simultaneously, before or after binding all of the analyte with a labelled monospecific antibody and the concentration of the analyte is then determined by measuring the label activity present in the solid phase in relation to a single point calibrator solution containing a known amount of the analyte substance.

12 Claims, No Drawings

AFFINITY IMMUNOASSAY SYSTEM

FIELD OF THE INVENTION

This invention relates to an assay system for quantitating components of interest in biological fluids.

BACKGROUND OF THE INVENTION

Immunoassays of various types have become the methods of choice for quantitating many substances of interest in biological fluids. All of the assays are quite similar in principle, but differ in the method for quantitating the amount of labelled substance bound to the analyte of interest.

In radioimmunoassay (RIA) either purified antigen or its specific antibody is labelled with a radioisotope, such as iodine-125 ($I^{125}$). A diagrammatic representation of the reaction mechanisms involved in the two main types of RIA are shown below.

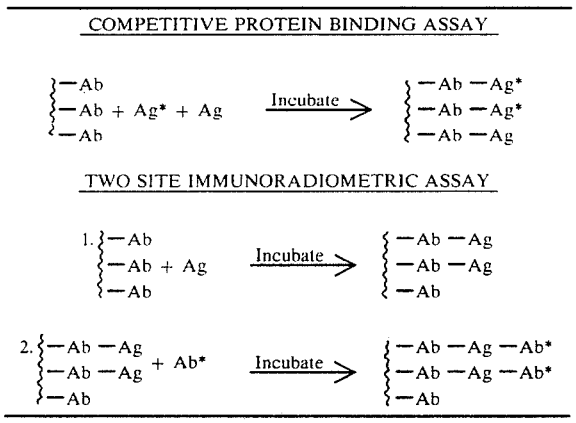

Key:
$\{$ = solid phase; Ab = antibody; Ag = analyte;
Ab* = labelled antibody; Ag* = labelled analyte.

In the competitive assay labelled and unlabelled analyte compete for binding sites on the antibody attached to the solid phase. After incubating, the solid phase is separated from the reaction mixture, and washed to remove residual unbound radioactivity. The amount of radioactivity bound to the solid phase is determined in a gamma counter. A standard curve is prepared using calibrator sera containing known amounts of analyte, and these are run simultaneously with the unknowns. A curve is generated and the unknowns are quantitated from the standard curve. In this case the amount of analyte in the unknown is essentially inversely proportional to the amount of radioactivity bound to the solid phase.

In the two site assay the analyte binds to the antibody attached to the solid phase. The solid phase is washed to remove residual unbound analyte and labelled antibody is added. During incubation the labelled antibody attaches to the analyte that is bound to the solid phase antibody. After incubation, the solid phase is washed to remove excess labelled antibody and the amount of radioactivity in the solid phase is determined. A standard curve is prepared using calibrator sera containing known amounts of analyte, and these are run simultaneously with the unknowns. A curve is generated and the unknowns are quantitated from the standard curve. In this case the amount of analyte in the unknown is essentially directly proportional to the amount of radioactivity bound to the solid phase.

A difficulty with these procedures is the limited assay range. That is, in the two site assay the standard curve only extends about two orders of magnitude, and in the competitive system two to three orders of magnitude. This phenomenon occurs because of the limited binding capacity of the solid phase antibody, and also the affinity constants of the antibody. Monoclonal antibodies have expanded the dynamic range of the assays to some extent, but many substances still require substantial dilution before they can be assayed in these systems.

Enzymeimmunoassays (EIA) operate in quite the same manner as RIA, except that an enzyme is used as a label instead of a radioisotope. Enzymes such as horseradish peroxidase, alkaline phosphatase, glucose oxidase and agalactosidase have been used as labels for antigens and antibodies in EIA systems. The reaction scheme below demonstrates a two site EIA using alkaline phosphatase (E) as a label.

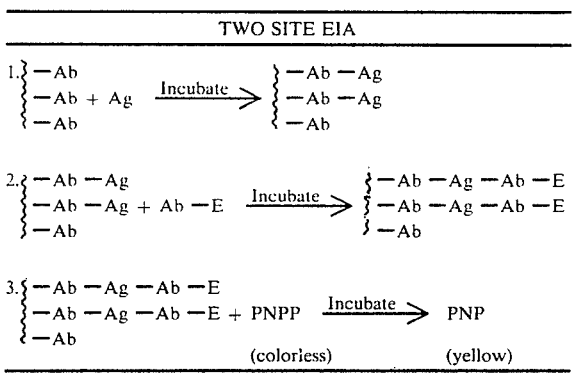

From the reaction sequence it can be seen that after binding of the enzyme-labelled antibody, the solid phase is washed to remove excess labelled antibody and is reacted with a substrate (PNPP) that the enzyme will degrade into a colored compound (PNP). The reaction is stopped by adding a chemical to poison the system and the amount of color is determined spectrophotometrically at a given wavelength. In this case the intensity of the color is directly proportional to the amount of analyte present in the sample in relation to a standard curve, as shown previously.

Fluoroimmunoassays (FIA) in many cases operate on the same basic principle as RIA and EIA, except that fluorescent compounds such as fluorescein, rhodamine and umbelliferone are used as labels. There are other types of FIA that operate on very different principles than those described above, since no solid phase is necessary. Examples of these types of assays are fluorescence polarization and fluorescence quenching.

There are several common difficulties inherent in RIA, EIA and FIA systems. One problem involves the limited dynamic range of the assays, as has been previously discussed. This limitation necessitates preparing multiple dilutions of each sample, as well as, a four-point standard curve. In addition these systems in many cases involve long incubation periods and several wash and reagent addition steps. All of these problems contribute to making the assays tedious, labortensive, time-consuming and costly in terms of reagent use.

All of the foregoing techniques, while sufficient to yield relatively accurate values for the analyte in question, are not entirely satisfactory, because they are either too sensitive, not sensitive enough, too laborious and time consuming or costly in terms of reagents.

SUMMARY OF THE INVENTION

It is therefore an object of this invention to provide a novel combination of reagents and a new method for using the reagents, which will overcome many of the aforementioned problems associated with the various types of immunoassays previously discussed.

Another object of the present invention is to provide a novel immunoassay system that has a very large dynamic and linearity range such that substances may be assayed over very large concentration ranges without the necessity of preparing multiple serial dilutions of the sample, or preparing a standard calibration curve.

A further object of the present invention is to provide a new type of immunoassay that reduces incubation times, is sensitive, precise and simple to perform, as well as, being cost-effective in terms of reagent use.

These objects are achieved by the disclosed invention, which is a novel affinity immunoassay that utilizes a solid phase nonimmunological group-specific ligand to isolate the analyte simultaneously, before or after binding with a labelled specific antibody.

DETAILED DESCRIPTION OF THE INVENTION

The present immunoassay system secures rapid, accurate determination of the concentration of analyte substances carried in a liquid medium over a very large concentration range through the use of a large excess of solid phase, nonimmunological, group-specific ligand which acts rapidly to bind substantially all of the analyte, in combination with the use of a large excess of labelled antibody monospecific to the analyte effective to combine with substantially all of the analyte, so that analyte present in the original solution is fixed to the solid ligand and each molecule of analyte is fixed to a labelled antibody. The solid phase ligand is readily separated from the liquid medium and carries with it the bound analyte and combined labelled antibody. Accordingly, the activity of the combined label on the solid phase is directly related to the amount of analyte in the sample being analyzed so that the amount of analyte in the sample may be determined as a direct proportion by comparison of this activity with the activity on the solid phase derived from a calibrator solution, or solutions of known concentration subjected to the same procedure.

In practicing the method of the present invention, the solid phase, nonimmunological, group-specific ligand may bind the analyte simultaneously, before or after the analyte is bound with a labelled specific antibody. The reaction mechanisms shown below demonstrate these alternative procedures.

A. SIMULTANEOUS REACTION (1) 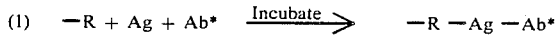

B. PRIOR ATTACHMENT OF ANALYTE TO SOLID PHASE AFFINITY LIGAND (1) 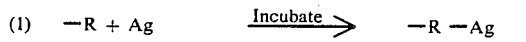

(2) 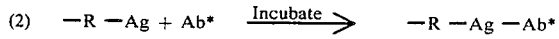

C. PRIOR REACTION OF ANALYTE WITH LABELLED ANTIBODY

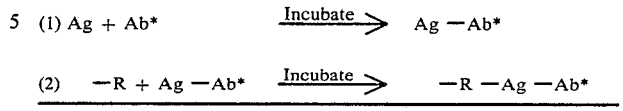

Key:
—R = solid phase group-specified ligand;
Ag = substance to be analyzed;
Ab* = labelled monospecific antibody against the substances to be analyzed.

In the simultaneous affinity immunoassay (Reaction A) the sample, labelled antibody and solid phase affinity ligand are added together and incubated until all of the analyte is bound by antibody and affinity ligand. The solid phase is then separated from the aqueous phase, washed and the amount of label present in the solid phase determined. A calibrator serum is also run, and as long as the concentration of analyte in the sample falls within the linearity range of the assay, the amount of analyte in the unknown will be directly proportional to the calibrator; and thus no standard curve is necessary.

In Reaction B the analyte is added to the solid phase affinity ligand incubated until all of the analyte is adsorbed. The labelled antibody is then added and is incubated until all of the bound analyte reacts with labelled antibody. The solid phase is separated, washed and the amount of label on the solid phase quantitated. Again, there is single-point calibration, and no standard curve required.

In Reaction C the analyte and labelled antibody are allowed to react until all of the analyte is bound by antibody. The solid phase affinity ligand is then added, and incubation is continued until all of the analyte-labelled antibody complex is adsorbed. The solid phase is separated, washed and the label on the solid-phase quantitated.

Solid phase ligands useful in the present invention are solids which may themselves have a group-specific, nonimmunological affinity for the analyte, for example, agar particles which have sulfate groups naturally occurring in the agar useful for bonding C-Reaction Protein (CRP) through mediation of calcium ion, or which may be solid bodies carrying group-specific, nonimmunological ligand material adhered to their surface, for example, Concanavalin A-Agarose useful for bonding glycoprotein, glycosylated hormones and glycosylated enzymes, hemoglobinpolyacrylamide useful for bonding haptoglobin, thyroxineagarose useful for bonding thyroxine binding globulin, agarose useful for bonding amyloid P component and chelated copper-zinc-agarose useful for bonding transferrin. Solid bodies carrying group-specific, nonimmunological ligand may be dispersible solids such as polyacrylamide, agarose or other beads or particles, or may be the walls of test tubes, cuvettes, tubes, microtitration wells, balls, magnetic compounds, strings or any other applicable solid to which ligands may be bound. Binding of the ligand to the solid body may be by passive adsorption, hydrogen, electrostatic or covalent bonding, either directly with the solid phase or via spacer arms or activating groups.

The antibody to be labelled for combination with the analyte may be polyclonal or monoclonal but must be monospecific for the compound to be assayed. For use in the present method, the antibody is, preferably, labelled with an enzyme for simplicity, stability, reliability and low cost. However, the antibody may be labelled with a fluorescent, chemiluminescent or bioluminescent compound or with a radioisotope.

Incubation for binding the analyte to the ligand and for combining the labelled antibody to the analyte is usually completed in from ten to fifteen minutes at room temperature. However, temperatures of from about 20 degrees to about 45 degrees C. may be used and the time of incubation may be longer or shorter depending on the temperature used and the sensitivity required. The pH in the reaction mixture is preferably from about 6.0 to about 8.0, but may be lower or higher depending on the label used and the characteristics of the analyte.

The novelties in the present invention are quite apparent and are as follows:

1. In all conventional immunoassays the solid phase contains an antibody specific for the analyte. They are total immunological systems. In the present affinity immunoassay the solid phase contains a non-immune ligand, which is group specific for the analyte but not monospecific, as is an antibody.
2. In this affinity immunoassay the reagent system uses an affinity ligand in combination with a monospecific antibody which confers the specificity to the assay.

The advantages of the affinity immunoassay system over conventional immunoassays are as follows:

1. The reactions with the affinity ligand are rapid as is the reaction with labelled antibody, thus reaction times are shortened.
2. By using a large excess of affinity ligand and labelled antibody, all of the analyte can be bound by both, allowing single point calibration. This situation makes the assay more cost effective in terms of reagent use and requires less labor, because a standard curve does not have to be constructed.
3. In conventional immunoassay systems the linearity and working range of the assay is limited in part by the amount and affinity constant of the antibody bound to the solid phase. In the present affinity immunoassay the limitation of the binding capability of the solid phase is governed strictly by the amount of ligand present. Since the ligand is in great excess in relation to the analyte, it can bind all of the analyte very quickly. Hence, the linearity range is extended substantially over conventional assay systems.
4. In this assay system, the user does not require expensive dedicated instruments to perform the assays.

The following examples show use of the present affinity immunoassay to assay for clinically important compounds. The examples are given to aid in understanding the invention, and are not meant to constitute the entire applicability of the method, nor should they be construed to be the only means in which the system may be used.

EXAMPLE 1

C-Reactive Protein (CRP) is an acute phase protein, normally present in human serum at a level of about 0.1–0.15 mg/dl. The level of CRP, however, rises rapidly in response to infection, surgery, trauma, malignancy and many other acute and chronic clinical situations.

CRP is usually assayed by latex agglutination, immunoprecipitation, immunoassay and reaction with C-polysaccharide. All of the methods suffer from one limitation or another. But, the affinity immunoassay system is well suited for this analysis, because of the relatively unique calcium binding properties of the molecule.

The following reagents are used in an affinity immunoassay using enzyme-labelled antibody:

1. Sulfated polyacrylamide beads, 80 to 150 micron diameter in a calcium buffer at pH 7.5.
2. Peroxidase-labelled anti human CRP antibody (Anti CRP-HPO).
3. Wash buffer at pH 7.5.
4. Buffered hydrogen peroxide-chromogen at pH 6.0.
5. 2.5 Normal sulfuric acid.
6. Calibrator serum containing a known amount of CRP.

Using the above reagents the following procedure is used to assay samples of material containing unknown concentrations of CRP:

1. Add 1.0 ml of sulfated polyacrylamide beads to each sample tube and to the calibrator tube.
2. Add 0.05 ml of each sample to the proper tube and 0.05 ml of CRP calibrator serum to the calibrator tube.
3. Add 0.1 ml of labelled antibody to each tube and incubate for 10 minutes at room temperature.
4. Separate the beads from the liquid phase and discard the liquid.
5. Add 5 ml of wash buffer to each tube, resuspend the beads, separate them from the liquid and discard the liquid.
6. Add 2.0 ml of buffered hydrogen peroxide-chromogen solution to each tube and agitate to suspend the beads. Incubate for 15 minutes at room temperature.
7. During the incubation period a yellow-orange color is formed. The enzyme reaction is stopped by adding 0.5 ml dilute sulfuric acid.
8. The beads are separated from the solution and the intensity of the color in each tube is determined by measuring the absorbance of the solution in a spectrophotometer.
9. As long as the absorbance of the analyte in the sample tubes falls within the predetermined linearity range of the assay, the concentration of CRP in each sample may be determined by the following equation.

$$CRP, mg/dl = \frac{(Conc.\ CRP\ in\ calibrator)\ (Absorbance\ of\ sample)}{Absorbance\ of\ calibrator}$$

This example utilizes the following reaction scheme:

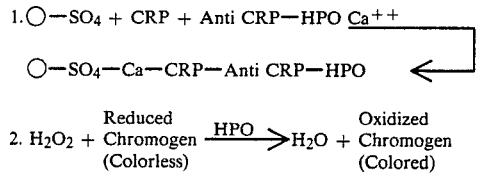

In reaction 1. the CRP simultaneously combines with HPO labelled antibody and with the solid phase sulfate groups. Binding of the CRP to the sulfate groups is mediated by $Ca^{++}$, which binds to CRP and the sulfate simultaneously. After all of the CRP is bound by labelled antibody and the solid phase sulfate groups, excess labelled antibody is removed by washing, and the solid phase is suspended in buffered H₂O₂-chromogen solution. The peroxidase catalyzes the reduction of H₂O₂ to water with simultaneous oxidation of the chromogen to a colored compound (Reaction 2.). The reaction is terminated by acid addition after an appropriate incubation period, the solid phase removed and the intensity of the color in each tube determined spectrophotometrically. The values for each sample are found by substituting the values obtained into the previously-cited equation.

EXAMPLE 2

In this example, the same reagents are used as in Example 1, but the CRP is affixed to the solid phase affinity ligand prior to addition of the labelled antibody.

Using these reagents, the following procedure is used to assay samples of material containing unknown concentrations of CRP:

1. Add 1.0 ml. of sulfated polyacrylamide beads to each sample tube and to the calibrator tube.
2. Add 0.5 ml. of each sample to the proper tube and 0.05 ml. of CRP calibrator serum to the calibrator tube.
3. Incubate the tubes for ten minutes at room temperature.
4. Separate the beads from the liquid phase and discard the liquid.
5. Add 5 ml. of wash buffer to each tube, resuspend the beads, separate them from the liquid and discard the liquid.
6. Add 0.1 ml. of labelled antibody to each tube and incubate for ten minutes at room temperature.
7. Separate the beads from the liquid and discard the liquid.
8. Add 5 ml. of wash buffer to each tube, resuspend the beads, separate them from the liquid and discard the liquid.
9. Add 2.0 ml. of buffered hydrogen peroxide-chromogen solution to each tube and agitate to suspend the beads. Incubate for fifteen minutes at room temperature.
10. During the incubation a yellow-orange color is formed. The enzyme reaction is stopped by adding 0.5 ml. dilute sulfuric acid.
11. The beads are separated from the solution and the intensity of the color in the tube is determined by measuring the absorbance of the solution in a spectrophotometer.
12. As long as the absorbance of the sample falls within the predetermined linearity range of the assay, the concentration of CRP in each sample may be determined by the same equation used in Example 1.

This example utilizes the following reaction scheme:

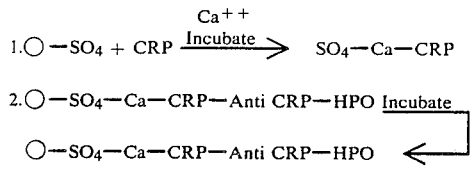

In reaction 1, the CRP binds to the sulfate groups on the solid phase via calcium. After all of the CRP is bound by the solid phase, the added labelled anti CRP antibody yields reaction 2 where the labelled antibody binds to the insolubilized CRP. Excess labelled antibody is removed by washing, and the solid phase is suspended in buffered H₂O₂-chromogen solution. The peroxidase catalyzes the reduction of H₂O₂ to water with simultaneous oxidation of the chromogen to a colored compound. The reaction is terminated by acid addition after an appropriate incubation period, the solid phase removed and the intensity of the color in each tube determined spectrophotometrically. The values for each sample are found by substituting the values obtained into the equation.

EXAMPLE 3

In this example, the same reagents are used as in Example 1, but the CRP is reacted with the labelled antibody prior to binding of the complex to the solid phase affinity ligand.

Using the same reagents as in Example 1, the following procedure is used to assay samples of material containing unknown concentrations of CRP:

1. Add 0.1 ml. of labelled antibody to each tube.
2. Add 0.5 ml. of each sample to the proper tube and 0.05 ml. of CRP calibrator serum to the calibrator tube.
3. Incubate the tubes for ten minutes at room temperature.
4. Add 1.0 ml. of sulfated polyacrylamide beads to each tube.
5. Incubate all tubes for ten minutes at room temperature.
6. Separate the beads from the liquid phase and discard the liquid.
7. Add 5 ml. of wash buffer to each tube, resuspend the beads, separate them from the liquid and discard the liquid.
8. Add 2.0 ml. of buffered hydrogen peroxide-chromogen solution to each tube and agitate to suspend the beads. Incubate for fifteen minutes at room temperature.
9. During the incubation, yellow-orange color is formed. The enzyme reaction is stopped by adding 0.5 ml. of dilute sulfuric acid.
10. The beads are separated from the solution and the intensity of the color in each tube is determined by measuring the absorbance of the solution in a spectrophotometer.
11. As long as the absorbance of the sample tubes falls within the predetermined linearity range of the assay, the concentration of CRP in each sample may be determined by the same equation used in Example 1.

This example utilizes the following reaction scheme;

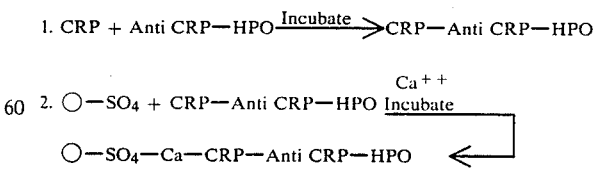

In reaction 1, the CRP binds to labelled antibody forming an antigen-antibody complex. After all the CRP is bound to antibody, the solid phase affinity ligand is added and yields reaction 2, wherein the antigen-labelled antibody complex binds to the solid phase via the CRP portion of the complex and calcium ion. Excess labelled antibody is removed by washing, and the solid phase is suspended in buffered $H_2O_2$-chromogen solution. The peroxidase catalyzes the reduction of $H_2O_2$ to water with simultaneous oxidation of the chromogen to a colored compound. The reaction is terminated by acid addition after an appropriate incubation period, the solid phase is removed and the intensity of the color in each tube determined spectrophotometrically. The values for each sample are found by substituting the values obtained in the above equation.

EXAMPLE 4

C3 is an important protein in the human complement system. Its two breakdown products play very important roles in the inflammatory response, phagocytosis, anaphylaxis and immune adherence of cell surfaces. Changes in C3 levels in a patient's serum are important and can offer the physician a clue to the clinical well-being of the patient in many disease states.

C3 is normally measured by immunoassay systems, such as radial immunodiffusion, nephelometry, RIA and EIA. All of these systems suffer from some procedural limitation or inconvenience to the user. The affinity immunoassay system provides an improved method, and takes advantage of the agarose binding property of C3.

The following reagents are used in an affinity immunoassay using enzyme-labelled antibody:
1. Agarose beads in a buffer.
2. Peroxidase-labelled anti human C3 antibody.
3. Wash buffer.
4. Buffered hydrogen peroxide-chromogen.
5. Dilute sulfuric acid.
6. Calibrator serum containing a known amount of C3.

Using the above reagents the following procedure is used to assay samples of material containing unknown concentrations of C3:
1. Add 1.0 ml. of buffered agarose beads to each tube.
2. Add 0.01 ml. of each sample to the proper tube and 0.01 ml. of calibrator serum to the calibrator tube.
3. Add 0.1 ml. of labelled antibody to each tube and incubate for 10 minutes at room temperature.
4. Separate the beads from the liquid phase and discard the liquid.
5. Add 5 ml. of wash buffer to each tube, resuspend the beads, separate them from the liquid and discard the liquid.
6. Add 2.0 ml. of buffered hydrogen peroxide-chromogen solution and agitate to resuspend the beads. Incubate for 15 minutes at room temperature.
7. During the incubation period a yellow-orange color is produced. The enzyme reaction is stopped by adding 0.5 ml. dilute sulfuric acid.
8. The beads are separated from the solution, and the intensity of the color in each tube is determined by measuring the absorbance of the solution in a spectrophotometer.
9. As along as the absorbances of the sample tubes fall within the predetermined linearity range of the assay, the concentration of C3 in each sample may be determined by the following equation:

$$C3, \text{mg/dl} = \frac{(\text{Mg/dl C3 in calibrator})(\text{Absorbance of sample})}{\text{Absorbance of calibrator}}$$

This example follows basically the same reaction sequences as does the CRP system previously described in Example 1, except for the differences in the solid phase affinity ligand.

I claim:

1. The affinity immunoassay system for determining the concentration of a sample of an antigenic or haptenic analyte dissolved in a liquid medium, said system comprising the steps of bringing said sample into contact with a body of solid phase, nonimmunological, group-specific ligand in an amount in excess of the amount of ligand required to bond of all said analyte, adding to and mixing said sample with a quantity of labelled antibody monospecific to said analyte in excess of the quantity of antibody required to bind all of said analyte incubating said sample under controlled conditions of time, temperature, p.H and reagent concentration to bind substantially all of said analyte to said ligand and to bind labelled antibody to substantially all of said analyte, separating said solid phase ligand carrying bound analyte and labelled antibody from said liquid medium, measuring the label activity carried by said solid phase and comparing the label activity carried by the solid phase ligand in assay of the sample with the label activity carried by the solid phase liquid from immunoassay of a calibrator serum containing a known concentration of analyte under the same conditions used in immunoassay of the sample according to the following equation:

Analyte, mg/dl =

$$\frac{(\text{Conc. Analyte in calibrator})(\text{Absorbance of sample})}{\text{Absorbance of calibrator}}$$

2. The affinity immunoassay system as defined in claim 1 in which said analyte and said antibody are added together for simultaneous contact with said solid phase ligand.

3. The affinity immunoassay system as defined in claim 1 in which said analyte is brought into contact with said solid phase ligand and is incubated to bind it to said ligand and said labelled antibody is then added and incubated until all the bound analyte is reacted with labelled antibody.

4. The affinity immunoassay system as defined in claim 1 in which said analyte and said labelled antibody are mixed and incubated until substantially all of the analyte is bound by antibody to form an analyte-labelled antibody complex and the incubated mixture is brought into contact with said solid phase ligand and incubated until substantially all of the analyte-labelled antibody complex is bound to said solid phase ligand.

5. The affinity immunoassay system as defined in claim 1 in which said antibody is labelled with an enzyme.

6. The affinity immunoassay system as defined in claim 1 in which said antibody is labelled with a radioisotope.

7. The affinity immunoassay system as defined in claim 1 in which said antibody is labelled with a fluorescent compound.

8. The affinity immunoassay system as defined in claim 1 in which said antibody is labelled with a bioluminescent compound.

9. The affinity immunoassay system as defined in claim 1 in which said antibody is labelled with a chemiluminescent compound.

10. The affinity immunoassay system as defined in claim 1 in which said ligand is carried on a solid body.

11. The affinity immunoassay system as defined in claim 1 in which said solid phase ligand is carried on a dispersible solid bead or particle.

12. The affinity immunoassay system as defined in claim 1 in which a standard curve is prepared using immunoassay data from a series of calibrator sera containing progressively greater known amounts of analyte under the same immunoassay conditions used in the immunoassay of the analyte sample, and the analyte concentration of the sample is determined by comparison of the label activity derived from the sample with said standard curve.

* * * * *